US012685608B2

(12) United States Patent
Heckel et al.

(10) Patent No.: US 12,685,608 B2
(45) Date of Patent: Jul. 21, 2026

(54) INVENTORY SYSTEMS AND METHODS FOR DETECTING AND COUNTING POTENTIALLY RETAINED SURGICAL ITEMS

(71) Applicant: Covidien LP

(72) Inventors: Donald W. Heckel, Green Bay, WI (US); Edward L. Brannan, Erie, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 19/350,637

(22) Filed: Oct. 6, 2025

(65) Prior Publication Data

US 2026/0026910 A1     Jan. 29, 2026

Related U.S. Application Data

(63) Continuation of application No. 18/558,453, filed as application No. PCT/IB2022/053823 on Apr. 25, 2022, now Pat. No. 12,433,711.

(60) Provisional application No. 63/183,092, filed on May 3, 2021.

(51) Int. Cl.
*A61B 90/00* (2016.01)
*A61B 90/98* (2016.01)
*G06K 7/10* (2006.01)

(52) U.S. Cl.
CPC .............. *A61B 90/08* (2016.02); *A61B 90/98* (2016.02); *G06K 7/10366* (2013.01); *A61B 2090/0804* (2016.02)

(58) Field of Classification Search
CPC ..... A61B 90/08; A61B 90/98; G06K 7/10366
USPC ......................................................... 235/451
See application file for complete search history.

(56) References Cited

U.S. PATENT DOCUMENTS

| | | | |
|---|---|---|---|
| 7,181,017 B1 * | 2/2007 | Nagel | H04L 9/302 |
| | | | 380/282 |
| 9,516,498 B2 * | 12/2016 | Miller, II | H04W 12/02 |
| 11,583,361 B1 * | 2/2023 | Roh | A61B 90/98 |
| 2008/0030345 A1 * | 2/2008 | Austin | G16H 40/63 |
| | | | 340/539.1 |

(Continued)

OTHER PUBLICATIONS

U.S. Prosecution file history of U.S. Appl. No. 18/558,453, now issued as U.S. Pat. No. 12,433,711.

*Primary Examiner* — Michael G Lee
*Assistant Examiner* — David Tardif
(74) *Attorney, Agent, or Firm* — Carter, DeLuca & Farrell, LLP

(57) ABSTRACT

An inventory system configured for detecting and counting potentially retained surgical items within a body of a patient includes a signal generator which generates an energizing signal for a first RFID tag affixed to a secure package or the second RFID tag affixed to a surgical item, an antenna operably coupled to the signal generator, a processor, and a memory. The antenna is configured to receive at least one of the first return signal transmitted by at least one of the first RFID tag or the second return signal transmitted by the second RFID tag. The memory includes instructions which when executed by the processor cause the system to energize the first RFID tag, receive from the antenna the first return signal including a first unique identifier, and generate a key based on the first unique identifier and a master private key stored on the memory.

20 Claims, 4 Drawing Sheets

(56) References Cited

U.S. PATENT DOCUMENTS

| | | | |
|---|---|---|---|
| 2010/0017224 A1* | 1/2010 | Kreiner | G08B 21/02 |
| | | | 340/572.1 |
| 2017/0312530 A1* | 11/2017 | Schilling | A61N 1/37223 |
| 2019/0206563 A1* | 7/2019 | Shelton, IV | G16H 50/20 |
| 2019/0290392 A1* | 9/2019 | Hansen | A61B 90/98 |
| 2020/0405311 A1* | 12/2020 | Shelton, IV | A61B 17/1155 |
| 2023/0023635 A1* | 1/2023 | Shelton, IV | G06F 13/4068 |

* cited by examiner

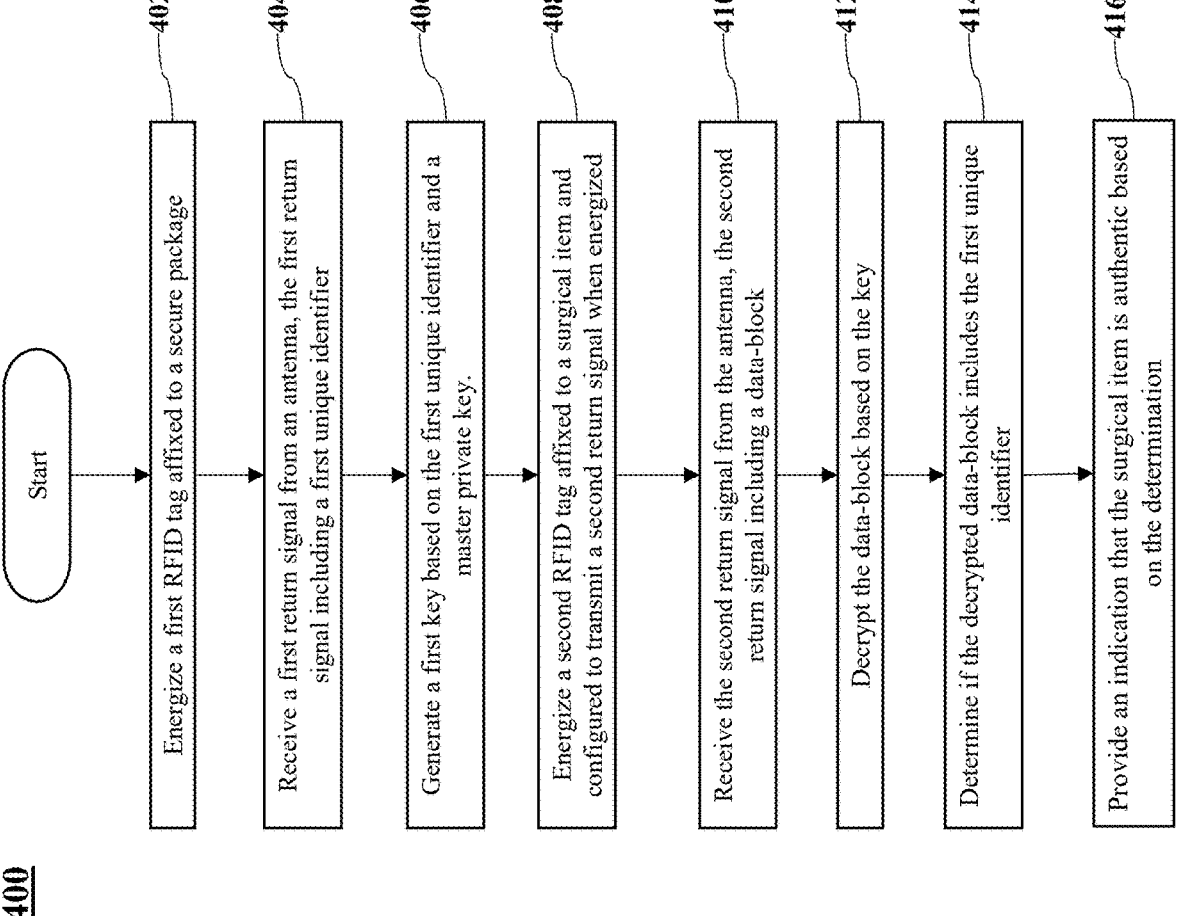

400

Start

402 — Energize a first RFID tag affixed to a secure package

404 — Receive a first return signal from an antenna, the first return signal including a first unique identifier 406 — Generate a first key based on the first unique identifier and a master private key.

408 — Energize a second RFID tag affixed to a surgical item and configured to transmit a second return signal when energized 410 — Receive the second return signal from the antenna, the second return signal including a data-block 412 — Decrypt the data-block based on the key 414 — Determine if the decrypted data-block includes the first unique identifier 416 — Provide an indication that the surgical item is authentic based on the determination

FIG. 4

INVENTORY SYSTEMS AND METHODS FOR DETECTING AND COUNTING POTENTIALLY RETAINED SURGICAL ITEMS

CROSS REFERENCE TO RELATED APPLICATIONS

This application is a continuation of U.S. patent application Ser. No. 18/558,453, filed on Nov. 1, 2023, now U.S. Pat. No. 12,433,711, which is a national stage application of PCT/IB2022/053823, filed Apr. 25, 2022, which claims the benefit, and priority to U.S. Provisional Patent Application No. 63/183,092, filed on May 3, 2021, the entire contents of each of which is hereby incorporated by reference.

FIELD

The present disclosure relates generally to interrogation and detection systems for radio-frequency (RF) tags, and more particularly, detection and inventory systems for potentially retained surgical items within surgical sites.

BACKGROUND

It is often useful to determine whether objects associated with a surgery are present in a patient's body before completion of the surgery. Such objects may take a variety of forms. For example, the objects may take the form of instruments, for instance, scalpels, scissors, forceps, hemostats, and/or clamps. Also, for example, the objects may take the form of related accessories and/or disposable objects, for instance, surgical sponges, gauzes, and/or pads. Failure to locate an object before closing the patient may require additional surgery, and in some instances, may have unintended medical consequences.

Accordingly, there is a need for a technology that is capable of providing both presence detection and tagged surgical item/implement identification functionality in the medical setting, as well as inventory controls of the tagged items/implements. Specifically, detecting the presence of, identifying, and maintaining inventory of tagged surgical items and materials that are used during the execution of a medical procedure. Technologies exist that enable these functions both individually as well as in conjunction with each other, but the methods and packaging of the discrete solutions used are not ideal for the application. More specifically, the components attached or affixed to the items being tracked are either too large physically and present nuisances or obstacles in the execution of the procedure, or the detection and identification performance of the solution may degrade rapidly in the presence of variable and uncontrolled dielectric or conductive materials.

Accordingly, there are needs for improvements in presence detection, tagged item identification, and inventory functionality in the medical setting.

SUMMARY

This disclosure relates to systems for detection of surgical objects and/or devices used in body cavities during surgery, specifically systems that include an antenna to be inserted directly into a surgical site to detect such surgical objects and/or devices.

In accordance with aspects of the disclosure, an inventory system is configured for detecting and counting potentially retained surgical items within a body of a patient. The inventory system includes a first RFID tag affixed to a secure package and configured to transmit a first return signal when energized, a surgical item configured to be removed from the secure package, a signal generator, an antenna operably coupled to the signal generator, a processor, and a memory. A second RFID tag is affixed to the surgical item. The second RFID is configured to transmit a second return signal when energized. The signal generator is configured to generate an energizing signal for at least one of the first RFID tag or the second RFID tag. The antenna is configured to receive at least one of the first return signal transmitted by at least one of the first RFID tag or the second return signal transmitted by the second RFID tag. The memory includes instructions stored thereon, which when executed by the processor cause the system to: energize the first RFID tag, receive the first return signal from the antenna, the first return signal including a first unique identifier, and generate a first key based on the first unique identifier and a master private key stored on the memory.

In an aspect of the present disclosure, the instructions, when executed by the processor, may further cause the system to energize the second RFID tag and receive the second return signal from the antenna, the second return signal including a data-block.

In another aspect of the present disclosure, the instructions, when executed by the processor, may further cause the system to decrypt the data-block based on the first key.

In yet another aspect of the present disclosure, the instructions, when executed by the processor, may further cause the system to determine if the decrypted data-block includes the first unique identifier.

In a further aspect of the present disclosure, the instructions, when executed by the processor, may further cause the system to provide an indication that the retained surgical item is authentic based on the determination or is not authentic based on the determination.

In yet a further aspect of the present disclosure, the instructions, when executed by the processor, may further cause the system to display on a display the indication that the surgical item is authentic based on the determination or is not authentic based on the determination.

In an aspect of the present disclosure, the master private key may include a unique key generated for a unique inventory system.

In yet another aspect of the present disclosure, the surgical item may include a second unique identifier. The instructions, when executed by the processor, further cause the system to link the first unique identifier of the first RFID, to the second unique identifier.

In a further aspect of the present disclosure, the instructions, when executed by the processor, may further encrypt the data-block which contains the unique identifier of the first RFID tag.

In yet a further aspect of the present disclosure, the instructions, when executed by the processor, may further include energizing the first RFID tag to enable the second RFID tag.

In an aspect of the present disclosure, a computer-implemented method for detection and inventory of potentially retained surgical items includes energizing a first RFID tag affixed to a secure package and configured to transmit a first return signal when energized, receiving a first return signal from an antenna, the first return signal including a first unique identifier, and generating a first key based on the first unique identifier and a master private key.

In accordance with aspects of the disclosure, the method may further include energizing a second RFID tag affixed to a surgical item and configured to transmit a second return signal when energized and receiving the second return signal from the antenna, the second return signal including a data-block.

In another aspect of the present disclosure, the method may further include decrypting the data-block based on the first key.

In yet another aspect of the present disclosure, the method may further include determining if the decrypted data-block includes the first unique identifier.

In a further aspect of the present disclosure, the method may further include providing an indication that the surgical item is authentic based on the determination.

In yet a further aspect of the present disclosure, the method may further include displaying on a display the indication that the retained surgical item is authentic based on the determination.

In an aspect of the present disclosure, the master private key may include a unique key generated for a unique inventory system.

In accordance with aspects of the disclosure, the method may further include linking a first unique identifier of the first RFID, to a second unique identifier of the surgical item.

In yet a further aspect of the present disclosure, the method may further include encrypting the data-block which contains the unique identifier of the first RFID tag.

In an aspect of the present disclosure, a non-transitory computer-readable storage medium in which is stored instructions for causing a processor to execute a computer-implemented method for detection and inventory of potentially retained surgical items is presented. The method includes energizing a first RFID tag affixed to a secure package and configured to transmit a first return signal when energized, receiving a first return signal from an antenna, the first return signal including a first unique identifier, and generating a key based on the first unique identifier and a master private key.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements and have been solely selected for ease of recognition in the drawings.

Various aspects of the presently disclosed antennae, RF tags, and articles containing them are described hereinbelow with reference to the drawings.

FIG. 4 is a block diagram of a computer-controlled method for detecting and counting potentially retained surgical items using the system of FIG. 1.

DETAILED DESCRIPTION

In the following description, certain specific details are set forth in order to provide a thorough understanding of disclosed aspects. However, one skilled in the relevant art will recognize that aspects may be practiced without one or more of these specific details or with other methods, components, materials, etc. In other instances, well-known structures associated with transmitters, receivers, or transceivers have not been shown or described in detail to avoid unnecessarily obscuring descriptions of the aspects.

Reference throughout this specification to "one aspect" or "an aspect" means that a particular feature, structure, or characteristic described in connection with the aspect is included in at least one aspect. Thus, the appearances of the phrases "in one aspect" or "in an aspect" in various places throughout this specification are not necessarily all referring to the same aspect. Furthermore, the particular features, structures, or characteristics may be combined in any suitable manner in one or more aspects.

Figure 1:
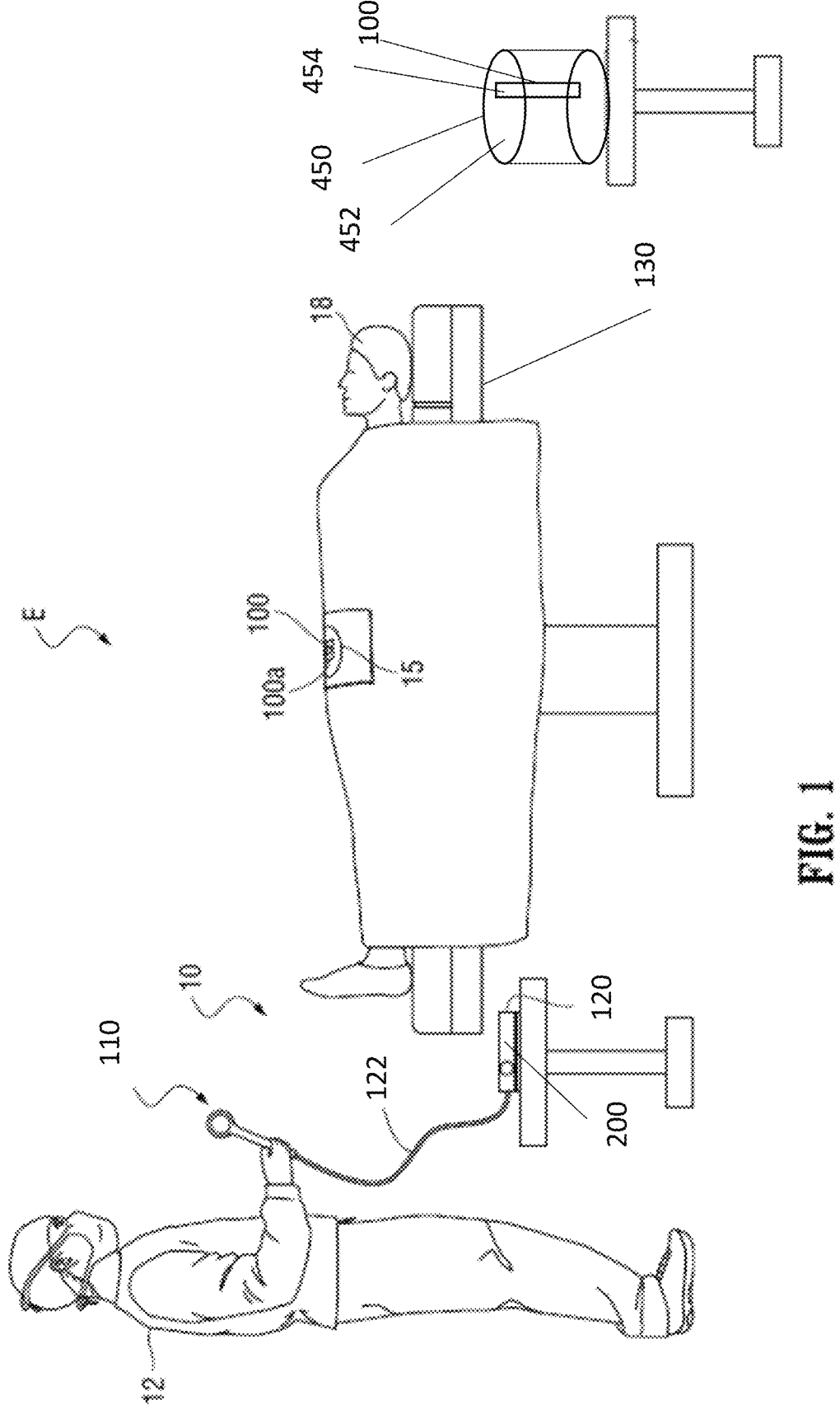
FIG. 1 is a schematic diagram showing a surgical environment illustrating a medical provider using an inventory system for detecting and counting an object within a patient that is tagged with an RFID tag according to one illustrated aspect.

FIG. 1 depicts a surgical environment "E" in which a medical provider 12 operates an inventory system 10 for detection and counting of radio-frequency identification (RFID) tags to ascertain the presence or absence of items, implements or objects 100*a* in a patient 18. The inventory system 10 may include a signal generator 120 and an antenna 110 coupled to the signal generator 120 by one or more communication paths, for example, coaxial cable 122. In one aspect of the inventory system 10, the antenna 110 may take the form of a hand-held wand 110*a*.

The object 100*a* may take a variety of forms, for example, instruments, accessories, and/or disposable objects useful in performing surgical procedures. For instance, the object 100*a* may take the form of scalpels, scissors, forceps, hemostats, and/or clamps. Also, for example, the objects 100*a* may take the form of surgical sponges, gauze, and/or padding. The object 100*a* is tagged, carrying, attached, or otherwise coupled to an RFID tag 100. Aspects of the inventory system 10 disclosed herein are particularly suited to operate with one or more RFID tags 100, which are not accurately tuned to a chosen or selected resonant frequency.

In use, the medical provider 12 may position the wand 110*a* approximate the patient 18 in order to detect the presence or absence of the one or more RFID tags 100 and hence an object 100*a*. The medical provider 12 may, in some aspects, move the wand 110*a* along and/or across the body of the patient 18. For a detailed description of an exemplary inventory system, reference may be made to commonly owned U.S. Patent Application Publication No. 2004/0250819 to Blair et al., entitled "Apparatus and Method for Detecting Objects Using Tags and Wideband Detection Device," filed Mar. 29, 2004, the entire contents of which is hereby incorporated by reference herein.

Figure 2:
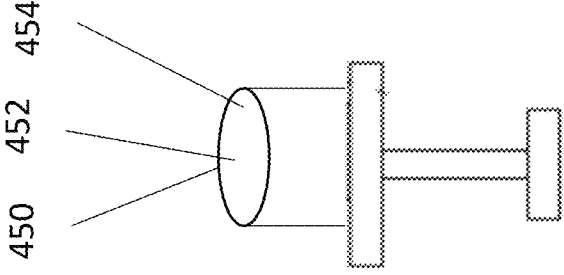
FIG. 2 is a schematic illustration of an antenna for detection of surgical implements within a patient's body in active use within a surgical site.
Figure 2:
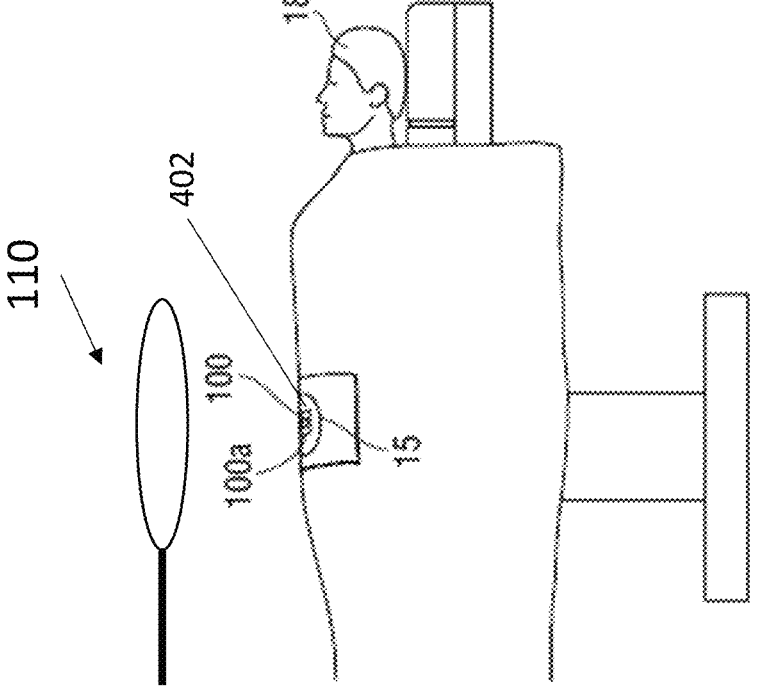

Referring now to FIG. 2, inventory system 10, for detection and counting of surgical implements (e.g., object 100*a*) within a patient's body, includes a signal generator 120 to provide an energizing signal for one or more RFID tags 100 (FIG. 1) affixed to an object 100*a* (FIG. 1). Each RFID tag 100 is configured to transmit a return signal when energized, such that an antenna 110 can detect the return signal and confirm the presence of objects 100*a* within the body of patient 18. The antenna 110 is operably coupled to the signal generator 120 via a communication cable 122 which may be of variable length to provide greater range of motion to the clinician handling the antenna 110. The signal generator 120 may include a controller 200.

In one aspect of inventory system 10, the antenna 110 is an antenna 110 configured to be waved over the surgical site 15, e.g., over the body of patient 18. For example, the antenna 110 may be held over the body of the patient 18 at the height of about four or about five inches while attempting to detect RFID tags 100 (e.g., first RFID tags 452 and/or second RFID tags 100), so that the user may detect confirm the presence of objects 100a within the body of patient 18.

The system 10 may further include a RFID-enabled secure package 450 (e.g., RFID-enabled smart packaging and/or RFID enabled secure mutual authentication packaging) which includes a first RFID tag 452 affixed thereto. For example, the first RFID tag 452 may be secured to a lid or a body of the RFID-enabled secure package 450. The first RFID tag 452 is configured to transmit a first return signal when energized. Generally, the RFID-enabled secure package 450 will include a surgical item 454 (e.g., cotton swabs) configured to be removed from the RFID-enabled secure package 450. The surgical item 454 includes a retained surgical item RFID tag, e.g., second RFID tag 100, affixed to the surgical item 454. The surgical item 454 may include, for example, any surgical sponge, cotton swab, instrument, tool, and/or device that is unintentionally left in the patient at the completion of a surgery or other procedure. The second RFID tag 100 is configured to transmit a second return signal when energized.

The RFID-enabled secure package 450 includes, but is not limited to, for example, caps, and closures and are generally configured to verify the contents of sealed containers to ensure the product is genuine, not part of a recall, within the expiration date, and/or has not been tampered with or diverted. RFID-enabled secure package 450 generally includes a packaging-secure mutual authentication RFID tag 452.

In aspects, the retained surgical item RFID tag 100 (the second RFID tag 100) may be linked to the secure package RFID tag 452 (the first RFID tag 452) by embedding an encrypted block of data that contains the unique identifier of the first RFID tag 452. For example, to enable the use of the retained surgical items 454, the first RFID tag 452 may be scanned by the antenna 110 in the inventory system 10.

Figure 3:
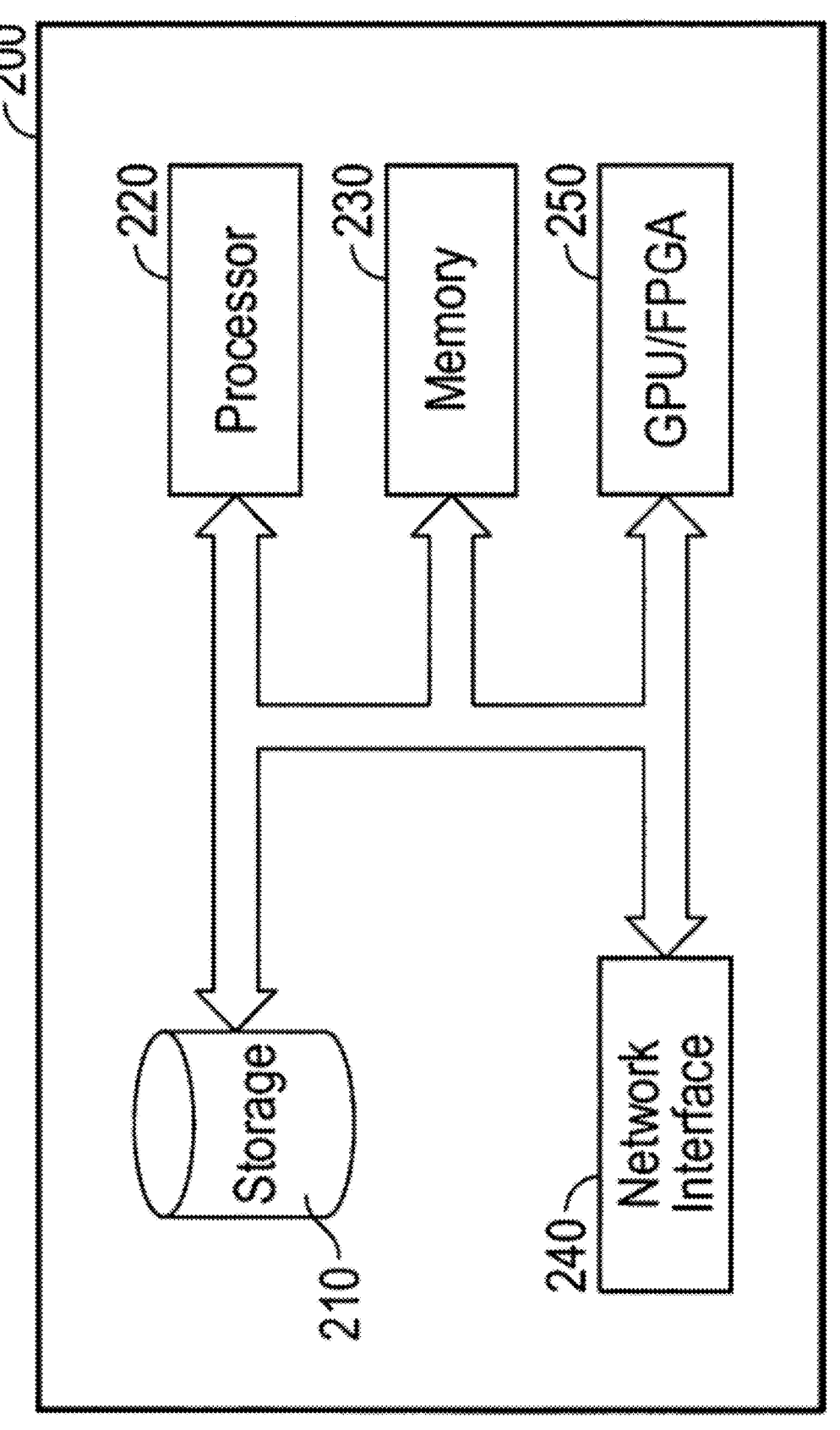
FIG. 3 is a block diagram of a controller of the system of FIG. 1.

FIG. 3 illustrates that controller 200 includes a processor 220 connected to a computer-readable storage medium or a memory 230. The computer-readable storage medium or memory 230 may be a volatile type of memory, e.g., RAM, or a non-volatile type of memory, e.g., flash media, disk media, etc. In various aspects of the disclosure, the processor 220 may be another type of processor such as, without limitation, a digital signal processor, a microprocessor, an ASIC, a graphics processing unit (GPU), a field-programmable gate array (FPGA), or a central processing unit (CPU). In certain aspects of the disclosure, network inference may also be accomplished in systems that have weights implemented as memristors, chemically, or other inference calculations, as opposed to processors.

In aspects of the disclosure, the memory 230 can be random access memory, read-only memory, magnetic disk memory, solid-state memory, optical disc memory, and/or another type of memory. In some aspects of the disclosure, the memory 230 can be separate from the controller 200 and can communicate with the processor 220 through communication buses of a circuit board and/or through communication cables such as serial ATA cables or other types of cables. The memory 230 includes computer-readable instructions that are executable by the processor 220 to operate the controller 200. In other aspects of the disclosure, the controller 200 may include a network interface 240 to communicate with other computers or to a server. A storage device 210 may be used for storing data.

Referring to FIG. 4, there is shown a flow chart of an exemplary computer-implemented method 400 for detection and inventory of potentially retained surgical items within surgical sites in accordance with aspects of the present disclosure. Although the steps of FIG. 4 are shown in a particular order, the steps need not all be performed in the specified order, and certain steps can be performed in another order. For simplicity, FIG. 4 will be described below, with the controller 200 performing the operations. However, in various aspects, the operations of FIG. 4 may be performed in part by the controller 200 of FIG. 3 and in part by another device, such as a remote server. These variations are contemplated to be within the scope of the present disclosure.

The two main functions of an inventory system (such as an operating room safety system) are to detect and count potentially retained surgical items (RSIs). The term retained surgical item, as used herein, includes any surgical sponge, instrument, tool, and/or device that is unintentionally left in the patient at the completion of a surgery or other procedure. The disclosed technology detects and counts potential RSIs, each of which includes an RFID, in a secure fashion and in a way that provides individual identification to each RFID based potential retained surgical item. The chain of trust allows the inventory system to authenticate that the RFID of the potential retained surgical item has been verified per requirements of the inventory system and that validation to intended use has occurred.

A benefit of the disclosed technology is that it does not require that the second RFID tag 100 have the capability to perform a cryptographic function such as mutual authentication to assess authenticity. For example, the second RFID tag 100 of a potential retained surgical item 454 may have limited memory space due to size, cost, or performance constraints yet could still be used in this system. Another benefit of the disclosed technology is that it provides a chain of trust to enable a high confidence of authenticity.

In aspects, the system may include an RFID-enabled secure package 450 (e.g., smart packaging) including a set of manufactured potential retained surgical items 454 (such as cotton sponges). The RFID-enabled secure package 450 includes a first RFID tag 452 (e.g., an RFID chip), which is capable of mutual authentication with a host (e.g., controller 200).

Initially, at step 402, the system 10 energizes the first RFID tag 452, which is affixed to the RFID-enabled secure package 450.

In aspects, the system may enable the second RFID tag 100 by performing a successful mutual authentication of the first RFID tag 452. This provides the first level of confidence that the packaging is authentic and may be used with the inventory system.

Next, at step 404, the system 10 receives a first return signal from the antenna 110 (FIG. 1). The first return signal includes a first unique identifier. The first unique identifier may include, for example, an identification code uniquely identifying the first RFID tag 452 of the RFID-enabled secure package 450.

In aspects, the first RFID tag 452 of the RFID-enabled secure package 450 may be programmed with unique derived keys based on the unique identifier of the first RFID tag 452. In cryptography, a derived unique key is a key management scheme in which for every transaction, a unique key is used which is derived from a fixed key. A key is a string of characters used within an encryption algorithm for altering data so that it appears random. A key locks (encrypts) data so that only a user with the right key can unlock (decrypt) the encrypted data.

Next, at step 406, the system 10 generates a first key based on the first unique identifier and a master private key. For example, the system 10 may generate a key based on a master private key and the UID of the first RFID tag 452 of the RFID-enabled secure package 450. The master private key may include a unique key generated for the specific inventory system. The first key may include a symmetric or asymmetric key. Symmetric encryption uses mathematical permutations to encrypt a plain text message. It also uses the same mathematical permutation, known as a key, to decrypt messages. Asymmetric encryption also uses mathematical permutations to encrypt a plain text message, but it uses two different permutations, still known as keys, to encrypt and decrypt messages. With asymmetric cryptography, a public key that can be shared with anyone gets used to encrypt messages while a private key that is known only by the recipient gets used to decrypt messages.

Next, at step 408, the system 10 energizes the second RFID tag 100 affixed to the surgical item 454. The second RFID is configured to transmit a second return signal when energized. For example, when scanning a potential retained surgical item, a derived key may be generated from a master private key, and the unique identifier (e.g., a 7 bit UID) of the first RFID tag 452 of the RFID-enabled secure package 450 is used to decrypt a data block of the second RFID tag 100 (e.g., the retained surgical item's RFID tag). For example, the retained surgical item data block may be as small as 128 bits in the case of Advanced Encryption Standard (AES) encryption in the low frequency, or high frequency retained surgical item RFID chip/tag. In aspects, the derived key may also be based on, for example, a random identifier (RID) and/or a non-unique identifier (NUID).

Next, at step 410, the system 10 receives the second return signal from the antenna 110. The second return signal includes a data-block. For example, the first RFID tag and/or the second RFID tag may include 1K of data. The data may be organized into sixteen sectors, and each sector may be organized into about four data-blocks. Each block of data may store sixteen bytes of data.

Next, at step 412, the system 10 decrypts the data-block based on the first key. Next, at step 414, the system 10 determines if the decrypted data-block includes the first unique identifier. For example, the decrypted data-block may include the 7 bit UID.

Next, at step 416, the system 10 provides an indication that the surgical item is authentic based on the determination. For example, if the decrypted surgical item data-block includes the unique identifier (e.g., the UID) of the secure authenticated packaging RFID chip/tag, the retained surgical item (e.g., cotton) is deemed authentic via a chain of trust.

For example, the system 10 may verify per operating room safety requirements and that validation of intended use of the surgical item has occurred.

In aspects, the system 10 may display, on a display, an inventory of potentially retained surgical items. For example, the system 10 may display the total number of surgical items and their status (e.g., retained and/or accounted for) and may provide an alert if any potentially retained surgical items are not accounted for.

While several aspects of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope of the claims appended hereto.

What is claimed is:

1. An inventory system configured for detecting and counting potentially retained surgical items within a body of a patient, the inventory system comprising:
   a first RFID tag affixed to a secure package and configured to transmit a first return signal when energized;
   a surgical item configured to be removed from the secure package, the surgical item including a second RFID tag affixed to the surgical item, the second RFID configured to transmit a second return signal when energized;
   a processor; and
   a memory, including instructions stored thereon, which when executed by the processor cause the system to:
      energize the first RFID tag;
      receive the first return signal, the first return signal including a first unique identifier of the first RFID tag; and
      generate a first key based on the first unique identifier and a master private key stored on the memory,
   wherein an encrypted data-block is embedded in the second RFID tag, the encrypted data-block containing the first unique identifier of the first RFID tag.

2. The system of claim 1, wherein the instructions, when executed by the processor, further cause the system to:
   energize the second RFID tag; and
   receive the second return signal, the second return signal including the encrypted data-block.

3. The system of claim 2, wherein the instructions, when executed by the processor, further cause the system to decrypt the encrypted data-block based on the first key.

4. The system of claim 3, wherein the instructions, when executed by the processor, further cause the system to determine if the decrypted data-block includes the first unique identifier of the first RFID tag.

5. The system of claim 4, wherein the instructions, when executed by the processor, further cause the system to provide an indication that the retained surgical item is authentic based on the determination.

6. The system of claim 5, wherein the instructions, when executed by the processor, further cause the system to display on a display the indication that the surgical item is authentic based on the determination.

7. The system of claim 1, wherein the master private key includes a unique key generated for a unique inventory system.

8. The system of claim 1, wherein the surgical item includes a second unique identifier, and
   wherein the instructions, when executed by the processor, further cause the system to link the first unique identifier of the first RFID, to the second unique identifier.

9. The system of claim 1, wherein the instructions, when executed by the processor, further include energizing the first RFID tag to enable the second RFID tag.

10. The system of claim 8, wherein the instructions, when executed by the processor, further cause the system to generate an inventory record that includes the first unique identifier and the second unique identifier, the inventory record being stored in the memory.

11. The system of claim 10, wherein the inventory record further includes a timestamp indicating when the surgical item was removed from the secure package.

12. The system of claim 10, wherein the inventory record is transmitted to a remote server over a secure communication link.

13. The system of claim 12, wherein the secure communication link utilizes an encrypted wireless protocol selected from the group consisting of Wi-Fi, Bluetooth Low Energy, and Zigbee.

14. The system of claim 1, wherein the antenna is configured as a handheld wand adapted to be swept across a surgical site for detecting potentially retained surgical items.

15. The system of claim 1, wherein the antenna is integrated into a surgical drape or mat positioned adjacent to the patient.

16. The system of claim 1, wherein the instructions, when executed by the processor, further cause the system to generate an alert signal when a number of RFID tags detected does not match an expected count of surgical items.

17. The system of claim 16, wherein the alert signal comprises at least one of an audible alarm, a visual display indicator, or a haptic feedback signal.

18. The system of claim 1, wherein the instructions, when executed by the processor, further cause the system to verify expiration date information stored in the encrypted data-block of the second RFID tag.

19. The system of claim 1, wherein the memory further includes instructions which, when executed by the processor, cause the system to prevent activation of the second RFID tag unless authenticity of the first RFID tag has been verified.

20. An inventory system configured for detecting and counting potentially retained surgical items within a body of a patient, the inventory system comprising:

a first RFID tag affixed to a package and configured to transmit a first return signal when energized;

a surgical item removable from the package, the surgical item including a second RFID tag configured to transmit a second return signal when energized;

a processor; and a memory, including instructions stored thereon, which when executed by the processor cause the system to:

energize the first RFID tag;

receive the first return signal, the first return signal including a first unique identifier of the first RFID tag; and generate a first key based on the unique identifier and a private key stored on the memory, wherein an encrypted data-block is embedded in the second RFID tag, the encrypted data-block containing the unique identifier of the first RFID tag, wherein the private key is configured for authenticating a relationship between the package and the surgical item.

* * * * *